(12) United States Patent
Kumar et al.

(10) Patent No.: US 6,967,250 B1
(45) Date of Patent: Nov. 22, 2005

(54) ENERGY TRANSFER DYES

(75) Inventors: Shiv Kumar, Belle Mead, NJ (US); Satyam Nampalli, Belle Mead, NJ (US); Mahesh Khot, Edison, NJ (US)

(73) Assignee: Amersham Biosciences Corp, Piscataway, NJ (US)

( * ) Notice: Subject to any disclaimer, the term of this patent is extended or adjusted under 35 U.S.C. 154(b) by 0 days.

(21) Appl. No.: 09/386,576

(22) Filed: Aug. 30, 1999

Related U.S. Application Data

(60) Provisional application No. 60/098,469, filed on Aug. 31, 1998.

(51) Int. Cl.$^7$ ............................................. C07D 265/36
(52) U.S. Cl. ...................... 544/105; 435/6; 549/223; 549/224; 549/227; 536/26.6
(58) Field of Search ........................... 544/105; 435/6; 549/223, 224, 227; 536/26.6

(56) References Cited

U.S. PATENT DOCUMENTS

| | | | | |
|---|---|---|---|---|
| 4,835,312 A | * | 5/1989 | Itoh et al. | 564/205 |
| 5,608,063 A | * | 3/1997 | Hobbs et al. | 544/244 |
| 5,688,648 A | * | 11/1997 | Mathies | 435/6 |
| 5,945,526 A | * | 8/1999 | Lee | 536/26.6 |

FOREIGN PATENT DOCUMENTS

| | | | |
|---|---|---|---|
| GB | 2 301 833 B | | 5/1996 |
| GB | 2301833 | * | 12/1996 |
| GB | 2341189 | * | 3/2000 |

OTHER PUBLICATIONS

Rosenblum, Nucleic Acids Research 25, 4500, 1997.*
Lee (Nucleic Acids Res 20, 2471, 1992).*
Auerbach, Joseph (Journal of Organic Chemistry 41(4), 725-6, 1976).*
Basha, Anwer (Tetrahedron Letters (17), 1465-8, 1977).*
Southwick et al., "Cyanine Dye Labeling Reagents—Carboxymethylindocyanine Succinimidyl Esters," *Cytometry* v. 11, pp. 418-430 (1990).
Mjumadar et al., "Cyanine Dye Labeling Reagents: Sulfoindocyanine Succinimidyl Esters," *Bioconjugate Chemistry*, v.4, pp. 105-111 (1993).
Waggoner and Ernst, "Fluorescent Reagents for flow Cytometry, Part 1: Principles of Clinical Flow Cytometry," (1993).
Koshkin et al., "Novel Convenient Synthesis of LNA [2.2.1] Bicyclo Nucleosides," *Tetrahedron Letters*, v. 39 pp. 4381-4384 (1998).
"Table of Contents of the Molecular Probes: Handbook of Fluorescent Probes and Research Chemicals", Molecular Inc. 6$^{th}$ Edition (1996).

* cited by examiner

*Primary Examiner*—David Lukton

(74) *Attorney, Agent, or Firm*—Richard J. Warburg; FOley & Lardner, LLP

(57) ABSTRACT

Energy transfer dyes, their preparation, and their use as labels in biological systems is disclosed. The dyes are preferably in the form of cassettes which enable their attachment to a variety of biological materials. The dyes and the reagents that can be made from them offer a wide variety of fluorescent labels with large Stokes' shifts enabling their use in a variety of fluorescence applications over a wide range of the visible spectrum.

7 Claims, 10 Drawing Sheets

FIGURE 2.

LIST OF BLUE ET-DYE TERMINATORS

| 5-FAM-Phe-5-TAMRA 5-FAM-Phe-5-ROX | 5-FAM-Phe-5-REG | 5-FAM-Phe-5-R110 |
|---|---|---|
| 11-ddGTP | 11-ddUTP | 11-ddGTP |
| 4-ddUTP | 11-ddATP | 11-ddUTP |
| 11-ddUTP | | 11-ddATP |
| | | 11-ddCTP |

ENERGY TRANSFER DYES

RELATED APPLICATION

This application claims the benefit of Kumar et al., U.S. Provisional Application 60/098,469, filed Aug. 31, 1998, entitled ENERGY TRANSFER DYES, which is hereby incorporated by reference in its entirety, including drawings.

FIELD OF THE INVENTION

The present invention relates to a novel class of energy transfer dyes, their preparation and their use as labels in biological systems.

BACKGROUND OF THE INVENTION

The following describes certain relevant art, none of which is admitted to be prior art to the appended claims.

Various methodologies are available for the visualization of cells or molecules in cells and for the measurement of analyte concentrations in fluids. Fluorescence microscopy utilizes fluorescent dyes, generally connected to specific probes, such as antibodies, for the localization of proteins and complexes in cells.

For the measurement of analyte concentrations, detection of an analyte of interest, determination of the particular sequence of a nucleic acid molecule, immunoassays and various hybridization methods have become popular over the last 40 years. Radioimmunoassays were developed because the high specific activity of the radionucleotide allowed measurement of very low concentrations of analyte. However, because of the concerns for the environment and human health, the use of radionucleotides in immunoassays is becoming less popular. The use of enzymes in immunoassays to amplify a signal has been a very important advance in the field of immunoassays because their use does not involve environmental or human health hazards or risks. Enzyme-linked immunoassays, however, can be problematic because the activity of the enzyme is temperature dependent and the instability of the enzyme or the substrates can result in inaccurate quantitation of the target ligand. Still other immunoassays monitor fluorescence as the signal, with or without enzymes, for the measurement of analyte concentrations.

Bi-fluorophore energy transfer dyes have been described which provide a novel methodology for monitoring processes in biological systems. The fluorescent nature of such dyes enables them to monitor processes in which the biological systems are involved. The fluorescent signal is measured by a fluorometer which is tuned to excite the fluorescent molecule at a specific wavelength and to measure the emission of fluorescence at another wavelength. The difference in the excitation and emission wavelengths is referred to as the Stokes shift.

Previously, a variety of combinations of bi-fluorophore dyes have been described. U.S. Pat. No. 5,688,648, entitled "Probes Labelled with Energy Transfer Coupled Dyes" Mathies et al., filed Dec. 19, 1995, which is incorporated herein by reference in it's entirety, including any drawings, discloses sets of fluorescent labels carrying pairs of donor and acceptor dye molecules wherein the labels can be attached to nucleic acid backbones for sequencing. Included is a method for identifying and detecting nucleic acids in a multi-nucleic acid mixture by using different fluorescent labels, wherein the fluorescent moieties are selected from families such as cyanine dyes or xanthenes. The fluorescent labels comprise pairs of fluorophores where one fluorophore donor has an emission spectra which overlaps the fluorophore acceptor's absorption so that there is energy transfer from the excited member to the other member of the pair.

UK Patent No. 2301 833 B entitled "Fluorescent Labelling Complexes with Large Stokes' Shifts Formed by Coupling Together Cyanine and Other Fluorochromes Capable of Resonance Energy Transfer" Waggoner et al., filed May 30, 1996, which is incorporated herein by reference in it's entirety, including any drawings, discloses complexes comprising a first fluorochrome having first absorption and emission spectra and a second fluorochrome having second absorption and emission spectra. The linker groups between the fluorochromes are alkyl chains. The fluorescent nature of the dyes enables them to be of use in sequencing and in nucleic acid detection.

In bi-fluorophore dye construction, aspects of particular importance are the distance between the acceptor and donor molecules, and the structure of the linker groups. There remains a need for additional improvements in dye construction, for example in order to accommodate selection of biological molecules of various sizes.

SUMMARY OF THE INVENTION

It has now been found that a novel class of energy transfer dyes are of use in labeling materials involved in sequencing reactions and other applications. The dyes are preferably in the form of "cassettes" which enable their attachment to a variety of biological materials. A cassette includes a covalently linked structure or complex with at least two fluorescent dye moieties, a linker group, and preferably a reactive group for attaching the complex to a biological material or other target material. The reactive group is chosen to be suitable for forming a covalent linkage with a functional group on a particular target material. The dyes are selected so the emission spectrum of one dye overlaps the absorption spectrum of a second dye, thereby allowing energy transfer to occur between the dyes. Dye cassettes containing aryl and heteroaryl linker groups provide stable, rigid structures to which biological molecules of various sizes may be linked, and which possess characteristics which allow for energy transfer between the fluorophores.

Accordingly, in one aspect the present invention provides an energy transfer dye of the formula (I):

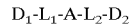

where $D_1$ is a first dye suitable as an acceptor or donor in an energy transfer arrangement, $D_2$ is a second dye that is suitable as a donor or acceptor in an energy transfer arrangement with the first dye, or any additional added dyes. A independently includes; (i) a chain that contains 5, and up to 20 linked atoms selected from carbon, sulfur, nitrogen, and oxygen, and/or (ii) one or more aryl, heteroaryl or other aromatic hydrocarbon groups, wherein the aromatic molecules contain cyclically linked atoms selected from carbon, nitrogen and oxygen. In this and/or in other aspects of the invention, when A is phenyl, it may or may not be linked directly to a carbonyl group. Preferably A comprises 5–20 linked atoms, wherein the linked atoms contain at least one cyclic group such as a carbocyclic or heterocyclic group, and wherein the atoms of the cyclic group are independently selected from the group consisting of carbon, nitrogen, sulfur, oxygen, and phosphorus.

The chain may optionally be substituted, if desired, with groups as known to those skilled in the art which do not prevent energy transfer, for example, the ring may be an aromatic or heteroaromatic ring substituted with one, two, or three substituents independently selected from the group consisting of alkyl, alkoxy, alkynyl, alkenyl, halogen, trihalomethyl, carboxylate, amino, nitro and ester moieties or substituted by $C_{1,2,3\text{ or }4}$ linear or branched alkyl, phenyl, or arylalkyl, optionally substituted with 1,2,3, or 4 substituents independently selected from OH, halo, methyl, hydrogen or ethyl groups.

$L_1$ and $L_2$ independently contain an atom or group adapted for attaching A to a biological molecule, and an atom or group of atoms for attaching to $D_1$ or $D_2$.

Additionally, $L_2$ independently contains an atom or group selectively adapted for attaching to an additional linker to which a third energy transfer dye is attached in a cascade energy transfer arrangement, wherein the third dye interacts with the second dye ($D_2$) which interacts with the first dye ($D_1$), and, an atom or group for attaching to a target material, e.g., a biological material as noted below.

When $D_1$ or $D_2$ are a fluorescein/rhodamine pair there are preferably 6 to 25 combined linked linker atoms in A, $L_1$ and $L_2$, and more preferably 9, 10, 11, 12, 13, 14, or 15 linker atoms. Preferably A is a $C_6$ aromatic hydrocarbon moiety linked to $L_1$ or $L_2$. $L_1$ is a $C_2$–$C_4$ hydrocarbon chain containing additional groups as known to those skilled in the art which allow binding to a xanthine or cyanine molecule, and $L_2$ is a $C_4$ hydrocarbon chain containing additional groups as known to those skilled in the art which allow binding to a xanthine or cyanine molecule and/or a biological target material.

The specification of a range of values for the number of atoms in a chain or group, whether an express listing of each integer within the range as above, or a description of the range by specifying the end points of the range, includes the specific description of each integer value within that range, including the endpoints. It further includes the specific description of each subrange within the larger range. For example, the range 1–6 includes the subranges 1–4 and 3–6, along with the other included subranges.

The reactive or functional group, $L_2$, may be any group suitable for attaching the energy transfer dye to a target material, preferably a target biological material and, as such, will be well known to those skilled in the art. Preferably the functional group of $L_2$ for attaching to a target material is selected from the group consisting of carboxyl, succinimidyl ester, sulpho-succinimidyl ester, isothiocyanate, maleimide and phosphoramidite, and groups covalently reactive with carboxyl, succinimidyl ester, sulpho-succinimidyl ester, isothiocyanate, maleimide and phosphoramidite.

Suitable dyes for $D_1$ or $D_2$ may be dyes which contain reactive or functional groups capable of linking with $L_1$ or $L_2$. The attachment groups of L, and $L_2$ may be any suitable adaptation for connecting to $D_1$ or $D_2$. Preferably the functional attachment group of $L_1$ and/or $L_2$ is $PO_3$, NH—CO or NH—CS.

The dye moieties, e.g., $D_1$ or $D_2$, of the present energy transfer dyes are fluorophores which are selected, as further indicated herein, to be able to participate in an energy transfer arrangement.

Preferably, the energy transfer dyes of this invention have a total molecular weight of less than 10,000 or 5,000 Daltons, more preferably less than 3,000 or 2,000 Daltons, still more preferably less than 1,500 or 1,200 Daltons.

In connection with the energy transfer dyes of the present invention, by "energy transfer arrangement" is meant that two fluorescent dyes are selected having absorption and emission spectra suitable for energy transfer between the dyes, and located with sufficient physical proximity and linkage such that photoexcitation of a first dye (the donor) results in the transfer of energy from the first dye to the second dye (the acceptor). Additional energy transfers involving one or more additional dye moieties can also be created.

Thus, an "energy transfer dye" refers to a fluorescent dye complex having at least two dye moieties which can participate in energy transfer between those two dye moieties, an energy transfer cascade arrangement would therefore involve more than two dye moieties and at least three dyes which can participate in energy transfer between the three dye moieties.

By "acceptor" in an energy transfer arrangement is meant a dye moiety which absorbs energy at a wavelength emitted by a donor dye moiety, i.e., the absorption spectrum of the acceptor overlaps the emission spectrum of the donor.

By "donor" in an energy transfer arrangement is meant a dye moiety which absorbs energy from light, and emits light at frequencies at least partially within the absorption spectrum of an acceptor dye moiety.

In the generic descriptions of compounds of this invention, the number of atoms of a particular type in a substituent group is generally given as a range. For example, an alkyl group containing from 1 to 4 carbon atoms. Such a range reference is intended to include specific references to groups having each of the number of atoms within the specified range including the endpoints. Other numbers of atoms and other types of atoms are indicated in the following manner, for example, $C_{1-4}$ includes each of $C_1$, $C_2$, $C_3$, and $C_4$ individually and any subgroup of the range.

Unless otherwise indicated, the term "alkyl" refers to a branched or unbranched aliphatic hydrocarbon group, preferably having from 1 to 6 carbon atoms, and more preferably 1 to 4 carbon atoms. Preferably the hydrocarbon group is saturated. The alkyl group may optionally be substituted, and some preferred substituents include alkoxy, alkylthio, halogen, amino, monosubstituted amino, disubstituted amino, and carboxy groups.

The term "lower alkyl" refers to an aliphatic hydrocarbon having 1 to 6 carbons, and preferably 1 to 4 carbon atoms. The lower alkyl group may optionally be substituted; preferred substituents include alkoxy, alkylthio, halogen, amino, monosubstituted amino, disubstituted amino, and carboxy.

The term "branched alkyl" refers to a branched aliphatic hydrocarbon. The branched alkyl group is preferably 3 to 10 carbons, and most preferably 3 to 6 carbons. The branched alkyl group may optionally be substituted and some preferred substituents include alkoxy, alkylthio, halogen (such as fluorine, bromine, chlorine, and iodine), amino, monosubstituted amino, disubstituted amino, and carboxy.

The term "haloalkyl" refers to a lower alkyl group which is substituted with a halogen. Thus, the term "fluoroalkyl" refers to a lower alkyl group which is substituted with a fluorine. The term "perfluoroalkyl" refers to a lower alkyl group which is substituted with a fluorine atom in every available position except for where the lower alkyl group is attached to the main chain.

The term "aryl" refers to an aromatic group which has at least one ring having a conjugated π electron system and includes both carbocyclic aryl (e.g., phenyl) and heterocyclic aryl groups (e.g. pyridine).

Specific examples of heterocyclic groups known in the chemistry arts include the following:

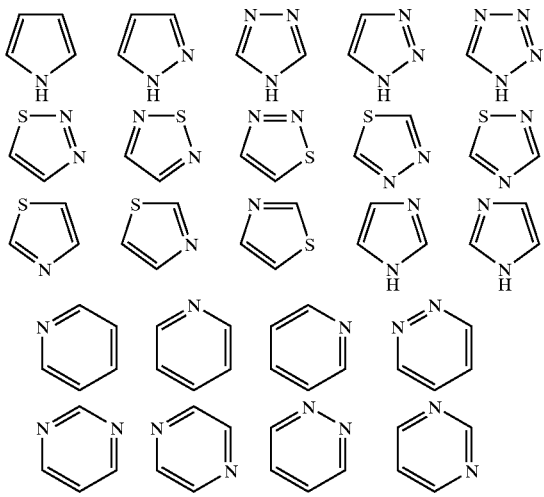

The aryl group is preferably 6 to 14 carbons, more preferably 6 to 10 carbons. Aryl moieties include monocyclic, bicyclic, and tricyclic rings, where each ring has preferably five or six members. The aryl moiety may be optionally monosubstituted or disubstituted independently with lower alkyl or alkenyl, alkynyl, hydroxyl, alkoxy, alkylthio, halogen, haloalkyl, mercapto, amino, monosubstituted amino, and disubstituted amino.

The term "carbocyclic" refers to a compound or group which contains one or more covalently closed ring structures, and that the atoms forming the backbone of the ring are all carbon atoms. The term thus distinguishes carbocyclic from heterocyclic rings in which the ring backbone contains at least one non-carbon atom. A "cycloalkane" or "cyclic alkane" or "cycloalkyl" is a carbocyclic group in which the ring is an optionally substituted cyclic aliphatic hydrocarbon, i.e., a cyclic alkyl group preferably with 3, 4, 5, or 6 ring carbons. Thus, a "cyclopropyl" group has 3 ring carbon atoms.

By "linear or branched alkyl" is meant a straight-chain or branched saturated aliphatic hydrocarbon. Typical alkyl groups include methyl, ethyl, propyl, isopropyl, butyl, isobutyl, tertiary butyl, pentyl, hexyl and the like. By halo is meant fluoro, chloro, bromo or iodo.

In the context of this invention, the term "target material" refers to a compound or structure to which a energy transfer dye is to be covalently attached or to which such a dye is attached.

By "biological material" is meant a compound produced by or present in an organism, including but not limited to polypeptides, nucleic acid molecules, carbohydrates, and lipids. Such compounds may be adapted or derivatised to include a group suitable for covalent attachment of an energy transfer dye. The term does not mean that the dyes of the present invention must be used with intact organisms, as often the dyes will be used with extracts, such as nucleic acid extracts, or samples, including preserved samples such as tissue sections, or in nucleic acid sequencing reactions. Preferably the size of the biological material is between 400 mw and 1,000,000 mw. More preferably the size is between 400 mw and 100,000 mw and most preferred the size is between 500 and 15,000 mw.

Preferably, the energy transfer dye is of the formula (I):

$$D_1\text{-}L_1\text{-}A\text{-}L_2\text{-}D_2.$$

Preferably, the donor dye is a xanthine or cyanine dye and the acceptor is a rhodamine or cyanine dye. Preferably $L_1$ and $L_2$ contain a reactive or functional group suitable for attachment of the dye to a corresponding functional or reactive group component of A. For example, for attachment of $D_1$ to the $L_1$ chain, dyes which contain a carboxyl or activated carboxyl group are preferred. The choice of reactive and functional group-containing dyes which are suitable for forming covalent linkages with the $L_1$ and/or $L_2$ chain will be well known to those skilled in the art. Additionally, the choice of reactive and functional group for $L_1$ and/or $L_2$ suitable for forming covalent linkages with chain A will be well known to those skilled in the art.

Suitable xanthine donor dyes include but are not limited to 5-carboxyfluorescein, 6-carboxyfluorescein, 6-carboxy-4',5'-dichloro-2',7'-dimethoxyfluorescein, CyA (3-(ε-carboxypentyl)-3'-ethyl-5,5'-dimethyl oxa-carbocyanine), Cy2 (3(ε-carboxypentyl)-3'-ethyl-oxa-carbocyanine) and Cy3 (3-(ε-carboxypentyl)-1'-ethyl-3,3,3',3'-tetramethyl-5,5'-disulphonato-carbocyanine.

Suitable cyanine dyes include, but are not limited to, Cy3.5 (3-(ε-carboxypentyl)-1'-ethyl-3,3,3',3'-tetramethyl-4,5,4',5'-(1,3-disulphonato)dibenzo-carbocyanine), Cy5 (1-(ε-carboxypentyl)-1'-ethyl-3,3,3',3'-tetramethyl-5,5'-disulphonato-dicarbocyanine, Cy5.5 (1-(ε-carboxypentyl)-1'-ethyl-3,3,3',3'-tetramethyl-4,5,4',5'-(1,3-disulphonato)-dibenzo-dicarbocyanine), Cy7 (1-(ε-carboxypentyl)-1'-ethyl-3,3,3',3'-tetramethyl-5,5'-disulphonato-tricarbocyanine). Cyanine dyes suitable for use in the energy transfer dyes of the present invention are disclosed in U.S. Pat. No. 5,268,486 (Waggoner et al.; incorporated herein by reference in its totality including any drawings).

Suitable rhodamine acceptor dyes include, but are not limited to; 5-carboxyrhodamine (Rhodamine 110-5), 6-carboxyrhodamine (Rhodamine 110-6), 5-carboxyrhodamine-6G (R6G-5 or REG-5), 6-carboxyrhodamine-6G (R6G-6 or REG-6), N,N,N',N'-tetramethyl-5-carboxyrhodamine, N,N,N',N'-tetramethyl-6-carboxyrhodamine (TAMRA or TMR), 5-carboxy-X-rhodamine, 6-carboxy-X-rhodamine (ROX), Cy3 (3-(ε-carboxypentyl)-1'-ethyl-3,3,3',3'-tetramethyl-5,5'-disulphonato-carbocyanine), Cy3.5 (3-(ε-carboxypentyl)-1'-ethyl-3,3,3',3'-tetramethyl-4,5,4',5'-(1,3-disulphonato) dibenzo-carbocyanine), Cy5 (1-(ε-carboxypentyl)-1'-ethyl-3,3,3',3'-tetramethyl-5,5'-disulphonato-dicarbocyanine, Cy5.5 (1-(ε-carboxypentyl)-1'-ethyl-3,3,3',3'-tetramethyl-4,5,4',5'-(1,3-disulphonato)-dibenzo-dicarbocyanine, and Cy7 (1-(ε-carboxypentyl)-1'-ethyl-3,3,3',3'-tetramethyl-5,5'-disulphonato-tricarbocyanine.

The above and additional dyes are described, for example, in Southwick et al., 1990, *Cytometry* 11:418–430; Mujumdar et al., 1993, *Bioconjugate Chemistry* 4:105–111; Waggoner and Ernst, Fluorescent Reagents for Flow Cytometry, Part 1: Principles of Clinical Flow Cytometry (1993) and *Molecular Probes Handbook of Flouresent Probes and Research Chemicals*, Molecular Inc. 6th edition (1996) Haugland, which are all incorporated herein by reference in their entirety including any figures.

Optionally the complexes may contain a third dye, e.g. a cyanine dye, attached to L2 through a suitable linker group and being in a cascade energy transfer arrangement with $D_1$ and $D_2$.

By "cascade energy transfer arrangement" is meant an energy transfer dye containing at least three dye moieties. In this type of arrangement the first dye is in an energy transfer arrangement with the second dye, wherein the second dye is the recipient of energy transferred from the first dye. Furthermore, in this type of arrangement the second dye is in an energy transfer arrangement in which it receives a transfer of energy from the first dye and also transfers energy to the third dye. Preferably, an additional linker is used to link the third dye to $L_2$ which is still available to attach to both $D_2$ and a biological material.

In a further aspect, the present invention relates to a biological material containing an energy transfer dye of the formula (I).

Suitable biological materials include, but are not limited to, antibodies, antigens, peptides, proteins, carbohydrates, lipids, peptide nucleic acids (PNA) nucleotides, oxy or deoxyribo polynucleic acids, Locked Nucleic Acids (LNA) as described in Koshkin, et al., Tetrahedron Letters 1998 39:4381–4384 and cells which may be derivatised, if necessary so that they contain one or more groups suitable for attachment of an energy transfer dye, e.g., amino, hydroxy, thiophosphoryl, sulphydryl or carboxy groups.

In another aspect, the present invention provides an energy transfer dye of the formula (II):

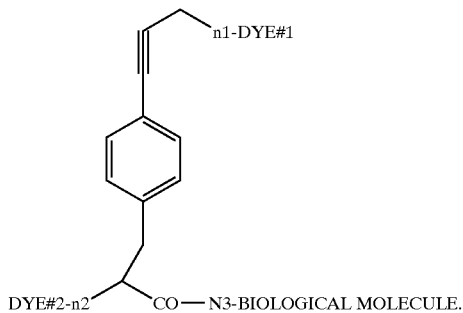

Preferably, dye 1 in this type of arrangement serves as the donor dye and includes those dyes selected from the groups consisting of xanthine or cyanine. Suitable dyes of either xanthine or cyanine have been discussed above. Additionally, in this type of arrangement Dye 2 serves as the recipient dye and includes those dyes selected from the groups rhodamine or cyanine as described above. Also preferred is that the aryl ring may be substituted with saturated or unsaturated side chains such as ethylenic group containing chains (C=C) or acetylenic group containg chains (C≡C).

n1, n2 and n3 are a chain of linked atoms wherein the atoms are selected from the group consisting of: carbon, oxygen, phosphorus, nitrogen and sulfur. Preferably the chain is composed of hydrocarbons and carbonyls. Preferably n1, n2 and n3 are NH.

In a further aspect the present invention provides an energy transfer dye of the formula (III):

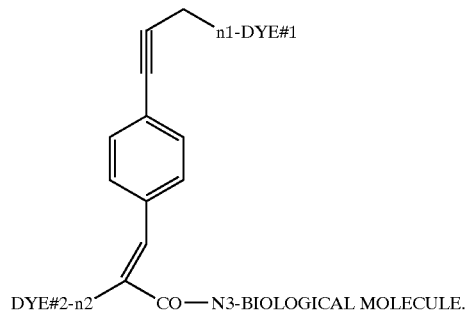

Preferably, dye 1 in this type of arrangement serves as the donor dye and includes those dyes selected from the groups consisting of xanthine or cyanine. Suitable dyes of either xanthine or cyanine have been discussed above. Additionally, in this type of arrangement dye 2 serves as the recipient dye and includes those dyes selected from the groups rhodamine or cyanine as described above. Further embodiments are included as described for arrangement II.

In a further aspect the present invention provides an energy transfer dye of the formula (IV):

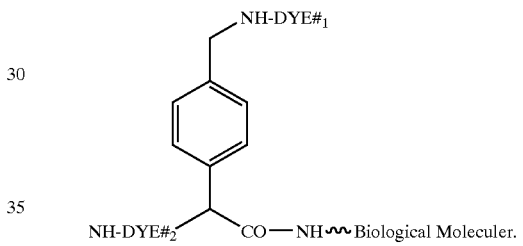

Preferably, dye 1 in this type of arrangement serves as the donor dye and includes those dyes selected from the groups consisting of xanthine or cyanine. Suitable dyes of either xanthine or cyanine have been discussed above. Additionally, in this type of arrangement dye 2 serves as the recipient dye and includes those dyes selected from the groups rhodamine or cyanine as described above. Further embodiments are included as described for arrangement II.

In a further aspect the present invention provides an energy transfer dye of the formula (V):

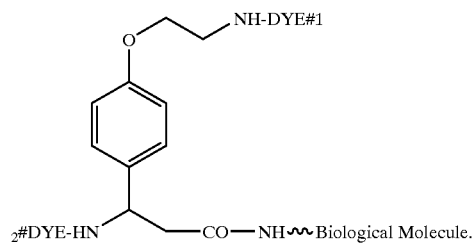

Preferably, dye 1 in this type of arrangement serves as the donor dye and includes those dyes selected from the groups consisting of xanthine or cyanine. Suitable dyes of either xanthine or cyanine have been discussed above. Additionally, in this type of arrangement dye 2 serves as the recipient dye and includes those dyes selected from the groups rhodamine or cyanine as described above. Further embodiments are included as described for arrangement II.

In a further aspect the present invention provides an energy transfer dye of the formula VI):

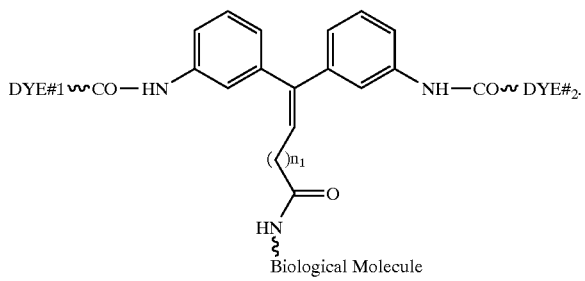

Biological Molecule

Preferably, dye 1 in this type of arrangement serves as the donor dye and includes those dyes selected from the groups consisting of xanthine or cyanine. Suitable dyes of either xanthine or cyanine have been discussed above. Additionally, in this type of arrangement dye 2 serves as the recipient dye and includes those dyes selected from the groups rhodamine or cyanine as described above. The group '$n_1°$' is preferably 1 to 10 linked hydrocarbons, and a further embodiment '$n_1$' equals one. Further embodiments are included as described for arrangement II.

In a further aspect, the present invention provides a method for the preparation of an energy transfer dye of the present invention preferably using at least five coupling reactions:
  (i) coupling A to a component of $L_2$;
  (ii) coupling the product of reaction (i) with $L_1$ which will be substituted by a reactive group suitable for forming the attachment with $D_1$;
  (iii) coupling the product of reaction (ii) with $D_1$;
  (iv) reacting the product of reaction (iii) such that $L_2$ is substituted by a reactive group suitable for forming attachment with $D_2$ and a biological molecule;
  (v) coupling the product of (iv) with $D_2$.

It would be readily apparent to one skilled in the art that alternative coupling steps could be used to the same end. One alternative, for example, would be to interchange $D_1$ with $D_2$ in steps i and iv.

In connection with the present energy transfer dyes and the attachment of the various moieties of those dyes, the term "coupling" refers to the formation of a covalent bond(s) linking two components, for example, linking a dye moiety with the $L_1$-A-$L_2$ portion of the energy transfer dye. The term "reacting" refers to the addition or removal of groups or components which results in the formation of a reactive group which can be readily attached to a covalent partner molecule.

As there may be several reactive groups present in any component taking part in one of the coupling reactions, it may be necessary for those not taking part in that reaction to be blocked or protected and then deprotected as appropriate later in the reaction sequence.

The dye will normally contain a substituent suitable for coupling reaction with the $L_1$-A-$L_2$ group or will be modified to contain such a group. For example, iodoacetamide is a suitable substituent for xanthine dyes, maleimido is a suitable substituent for cyanine dyes.

The fluorescent energy transfer dyes may be used to form reagents by covalently binding the dyes to carrier materials such as polymer particles, cells, glass beads, antibodies, proteins, peptides, enzymes, carbohydrates, lipids and nucleotides or nucleic acids (DNA, PNA, LNA (Locked Nucleic Acids, "Novel convenient Syntheses of LNA [2.2.1] Bicyclo-Nucleosides", Koshkin et al., *Tetrahedron Letters* 39:4381–4384 (1998)) and RNA) and analogues which contain or have been derivatised to include at least one first reactive group capable of forming a covalent bond with the functional group on the labeling complex (or functional group capable of forming a covalent bond with a reactive group on the complex, as described above) and at least one second reactive group (or functional group, as the case may be), having specificity for, and being capable of forming a covalent bond with, a target biological compound, such as antibodies, cells, drugs, antigens, bacteria, viruses and other micro-organisms.

When the carrier has functional groups, the functional groups may be antibody or DNA suited for attachment to antigen or a complementary DNA sequence, respectively. When the carrier material has reactive groups, the carrier may be a polymer particle or an antigen suitable for attachment to DNA or an antibody for example. Techniques for covalently binding fluorochromes to carrier materials such as those mentioned are well known in the art and readily available in the literature.

The carrier material can further include nucleotides derivatised to contain one of amino, sulphydryl, carboxyl, carbonyl or hydroxyl groups, and oxy or deoxy-ribo polynucleic or nucleic acids derivatised to contain one of amino, thiophosphoryl, sulphydryl, carboxyl, carbonyl or hydroxyl groups.

The functional groups on the carrier material which are complementary to i.e. capable of forming covalent bonds with, the reactive groups of the labeling complexes of the invention include amino, carboxyl, carbonyl and hydroxyl groups.

The present invention also relates to labeling processes in which, in a first step, an energy transfer dye of the present invention covalently reacts with and thereby labels a first component and then uses the labeled first component to bind with a second component to form a labeled second component. Suitably, the first component may be one member of a specific binding pair, (a specific binding partner). In the second step of the procedure, the fluorescently labeled specific binding partner is then used as a probe for binding to a second member of the specific binding pair (the second component) for which it has specific affinity.

The specific binding pairs may include a wide variety of molecules which are arbitrarily termed ligands and receptors. An example of such ligand-receptor pairs includes an antibody and the corresponding antigen for which the antibody is specific. When the target of the so-labeled antibody is a cell, the second step of the procedure may be used to determine the amount of labeled antibodies which are attached to that type of cell by determining the intensity of the fluorescence of the cells. By this procedure, monoclonal antibodies and other components covalently labeled in a first step with the fluorescent compounds of the present invention could be used as antigen probes.

Numerous other examples are known to those skilled in the art. Thus, additional ligand-receptor pairs include, for example, biotin-(strept)avidin, hormone receptor-hormone, DNA-complementary DNA, DNA-RNA, DNA-binding protein, enzyme-substrate, and the like. It is to be understood that any two molecules which possess a specific binding affinity may be employed, so that the energy transfer dyes of the present invention may be used for labeling one member of a specific binding pair which in turn may be used in the detection of the complementary member.

In an additional embodiment the present invention features a method for determining the nucleotide base sequence of a DNA molecule consisting of the steps of incubating a DNA molecule annealed with a primer molecule able to hybridize to the DNA molecule in a vessel containing a thermostable DNA polymerase, a energy transfer dye attached to a DNA sequencing terminator, wherein the attachment is with a linker of at least 5, and more preferably at least 10 atoms between the dye and the nucleotide, and separating DNA products of the incubating reaction according to size whereby at least a part of the nucleotide base sequence of the DNA molecule can be determined. Such a method is described in example III and FIGS. 7 and 8 provide sequence data and an exemplary set of energy transfer dye terminators.

In preferred embodiments, the energy transfer dye terminator is a compound selected from the group consisting of 5-FAM-Phe-5-REG-11-ddUTP,: 5-FAM-Phe 5-REG-11-ddCTP: 5-FAM-Phe-5-REG-11-ddATP: 5-FAM-Phe-5-REG-11-ddGTP, 5-FAM-Phe-5-ROX-11-ddCTP, 5-FAM-Phe-5-ROX-11-ddUTP, 5-FAM-Phe-5-ROX-11-ddATP, 5-FAM-Phe-5-ROX-11-ddGTP, 5-FAM-Phe-5-TAMRA-11-ddGTP, 5-FAM-Phe-5-TAMRA-11-ddATP, 5-FAM-Phe-5-TAMRA-11-ddCTP, 5-FAM-Phe-5-TAMRA-11-ddUTP, 5-FAM-Phe-5-R110-11-ddATP, 5-FAM-Phe 5-R110-11-ddUTP, 5-FAM-Phe-5-R110-11-ddGTP, or 5-FAM-Phe-5-R110-11-ddCTP.

In accordance with conventional usage, the abbreviations used in the preceding paragraph have the following meanings:

FAM=5 or 6-carboxyfluorescein
REG=5 or 6-carboxyrhodamine, 6G
TAMRA=5 or 6-carboxytetramethylrhodamine
ROX=5 or 6-carboxy-X-rhodamine U.S. patent application entitled "Dideoxy Dye Terminators, Ser. No. 09/018,695 filed Feb. 4, 1998, and which is herein incorporated by reference in its' entirety including any drawings, describes the importance of the length of the linker between dye and the ddNTP. The construction and attachment of various linkers is well known in the art. Suitable reagents for linker construction include one or more compounds consisting of activated forms of amino-protected alkyl or aryl amino acids such as compounds of the formula R—NH—$(CH_2)_n$—$CO_2R'$ or R—NH(CH $_2)_n$—X $(CH_2)_m$—$CO_2R'$, where R is an acid- or base-labile protecting group, R' is a reactive ester or anhydride group, X is aryl, O, S, or NH, and where n and m are 0–12. Other linkers constructed by N- or O- or S-alkylation are also suitable. The exact linker length for a specific dye and dideoxynucleotide combination can be determined empirically by monitoring band uniformity in DNA sequencing.

Other features and advantages of the invention will be apparent from the following description of the preferred embodiments thereof, and from the claims.

BRIEF DESCRIPTION OF THE FIGURES

FIG. 2 is a table of blue ET Dye Terminators.

Figure 1:
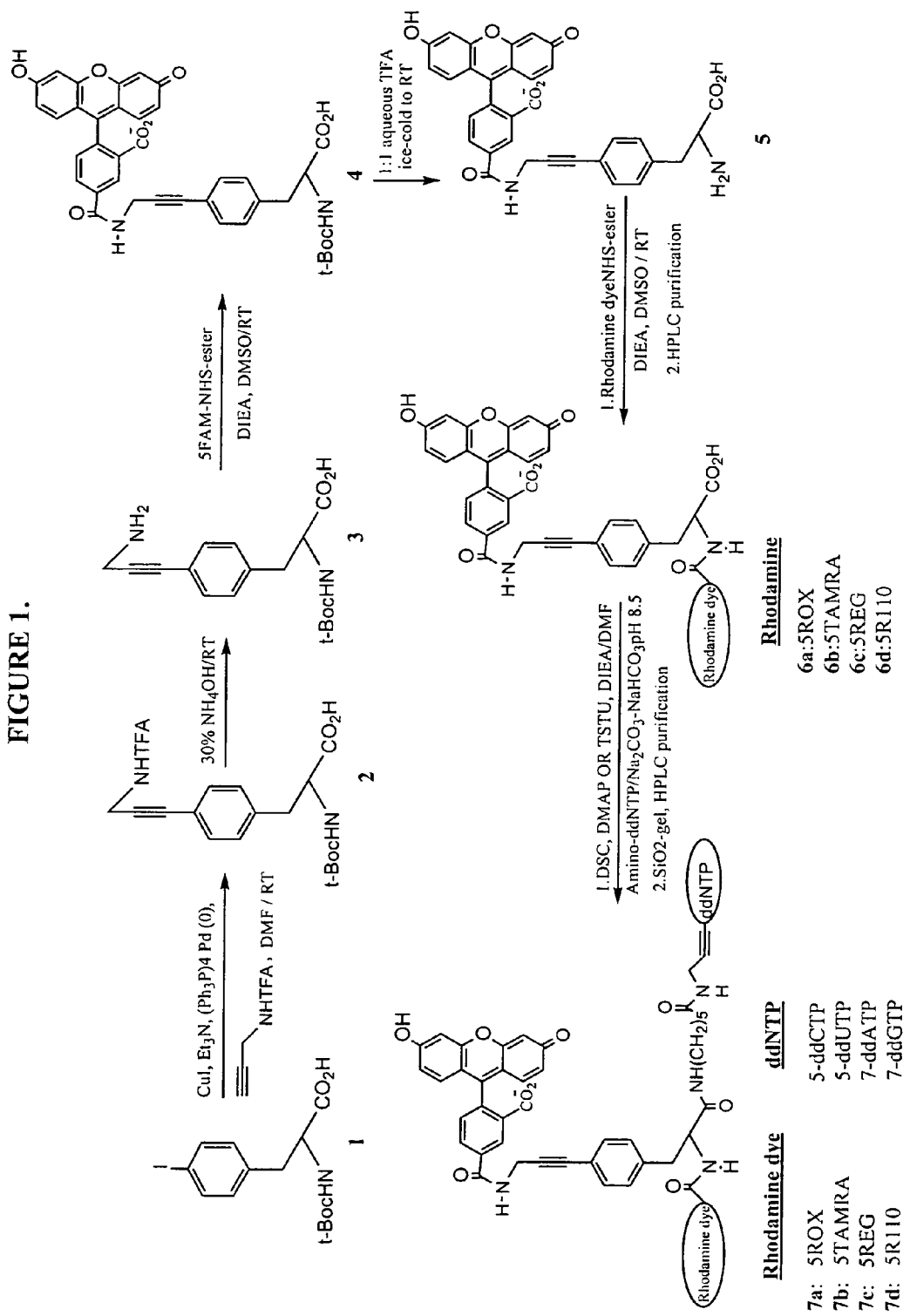
FIG. 1 is a schematic of the reaction for preparing Energy Transfer (ET) dye terminator cassette, N-5ROX-p-propargylamido-5FAM-L-phenylalanine-11-ddCTP (5FAM-ROX-Phe-11-ddCTP) and other terminators of the invention.

The drawings are not necessarily to scale, and certain features of the invention may be exaggerated in scale and shown in schematic form in the interest of clarity and conciseness.

DESCRIPTION OF THE PREFERRED EMBODIMENTS

This invention relates to novel energy transfer dyes which exhibit fluorescence energy transfer (donor-acceptor energy transfer). These novel energy transfer dyes can be tuned to specific excitation and emission wavelengths to accommodate a wide variety of assay or visualization systems. Assays such as molecular hybridization between moieties such as nucleic acids or proteins, or for procedures such as sequencing or electrophoresis of small cellular components.

The energy transfer dyes of the present invention provide a valuable set of fluorescent labels which are particularly useful for multiparameter analysis and importantly, are sufficiently low in molecular weight to permit materials labeled with the fluorescent complexes to penetrate cell structures. As such, the dyes are well suited for use with DNA, PNA, LNA and/or RNA probes. Multiparameter analysis can be performed on multiple samples to detect the presence of target biological compounds. Each sample is labeled by well known labeling methods with a energy transfer dye.

For example, one sample (sample 1) suspected of containing a target biological compound is incubated with a single fluorochrome, such as fluorescein, Cascade Blue, a BODIPY dye, or one of the monomethine rigidized dyes, or $CY3(SO_3)_2$, all emitting in the 500–575 nm wavelength range (green to orange). A second sample suspected of containing the target biological compound (the same compound or a different compound as that in sample 1), is incubated with an energy transfer dye of the invention, for example N-5-tetramethyl-Rhodamine-p-propargylamido-5FAM-L-phenylalaine, which will absorb light at 490 nm and emits fluorescence in the range 525 nm–602 nm, depending on the Rhodamine dye selected. Additional samples suspected of containing another target compound are incubated with other dyes of the invention have different absorbence and emission spectra than dyes already used in the assay. After a suitable period to permit the fluorescent labels to bind with the target compounds, unbound label is removed by washing and the labeled samples are mixed.

Detection is possible with a single wavelength excitation source, i.e. at laser line 488 nm. Each differently labeled sample will fluoresce a different color at the emission wavelength of its particular label, allowing the individual labels to be distinguished from each other.

Those skilled in the art will recognize that the fluorescent energy transfer labeling dyes of the present invention can be used for a variety of immunofluorescence techniques, including direct and indirect immunoassays, and other known fluorescent detection methods. The conditions of each labeling reaction, e.g. pH, temperature and time are known in the art, but generally room temperature is preferred. The pH is adjusted depending on the optimum reaction conditions for the particular reactive groups according to known techniques.

The energy transfer dyes of the present invention and the reagents that can be made from them offer a wide variety of fluorescent labels with large Stokes' shifts. The Stokes shift of the dye should be as large as possible to minimize the measurement of noise from the excitation source so that the signal-to-noise ratio at the limit of sensitivity is maximized. The availability of dyes with Stokes shifts greater than 100 nm is greatly limited. To further limit the usefulness of available dyes, the solubility of the dyes in aqueous samples can be a problem because most dyes with large Stokes shifts are water insoluble. The problem of a dye possessing a small Stokes shift is usually overcome in the engineering of the fluorometer by the use of monochromators or expensive optics which filter out the light from the excitation source. However, to overcome the loss in light intensity due to the filters, for example, one requires the use of high powered light sources. These light sources produce heat which must be dissipated in an instrument by using heat sinks or fans.

Fluorescent dye molecules incorporated into or onto particles will exhibit fluorescence quenching because of the close proximity of the dyes to each other and to the matrix of the particle. The dyes are positioned in the ET-cassette at an energy exchanging distance from one another which allows donor-acceptor energy transfer. Moreover, the aryl linker provides a rigid backbone which is adapted to provide particular distance between the fluorophores. Additionally, this linker allows for the attachment of the ET-cassette to a wider variety of biological molecules, varieties such as those described above.

Those in the art will appreciate that the dyes of the invention can be used in a variety of fluorescence applications over a wide range of the visible spectrum. Also, those in the art would recognize that more than one dye pair which exhibits fluorescence energy transfer can be incorporated into or onto molecules resulting in a class of compounds which fluoresce at different wavelengths. In addition, with the inventive teachings described herein, incorporation into or onto molecules of 3 or more dyes, which together provide a cascade of energy transfer from the absorber to the intermediate donor to the acceptor (which fluoresces), can result in the production of compounds with very long Stokes shifts and allows one to produce compounds with nearly an unlimited variety of excitation and emission characteristics.

EXAMPLES

The following examples serve to illustrate the preparation of the energy transfer dyes of the present invention. These examples are in no way intended to limit the scope of the invention.

Example 1

Preparation of FAM Phenylalanine-Linker Rhodamine Energy Transfer Cassette 1.1) Preparation of N-Boc-ρ-N-propargyltrifluoroacetamido-L-phenylalanine To a stirred suspension of N-Boc-ρ-iodo-L-phenylalanine (1.0 g, 2.55 mmol) and CuI (97 mg, 0.5 mmol, 0.2 eq) in anhydrous DMF (20 ml), under Ar were added N-propargyltrifluoroacetamide (1.16 g, 7.67 mmol, 3 eq), triethylamine (0.71 mL, 5.1 mmol, 2 eq) and tetrakis (triphenylphosphine) Pd(0) (295 mmol, 0.1 eq). The reaction was allowed to proceed for 6 hours. The mixture was then diluted with 1:1 MeOH—$CH_2Cl_2$ and treated with AGI X 8 resin (Bio-Rad) for 15 minutes, then filtered and the resin was washed with 1:1 MeOH—$CH_2Cl_2$. The combined filtrates were concentrated under reduced pressure and the residue obtained was adsorbed on a silica gel for column chromatography. Elution with 5–15% MeOH in $CHCl_3$ gave N-Boc-ρ-N-propargyltrifluoroacetamido-L-phenylalanine. $^1$H-NMR ($CD_3OD$)δ 7.31 (d, J=6.7 Hz, 2H, Ar), 7.19 (d, J=6.7 Hz, 2H, Ar), 6.49 (broad s, 1H, NH-Boc), 4.28 (broad s, 2H, $CH_2$-propargylic$_2$), 4.21 (m, 1H, CH-chiral), 2.84–3.25 (m, 2H, $CH_2$-phe), 1.38 (s, 9H, t-butyl).

1.2) Preparation of N-Boc-ρ-propargylamino-L-phenylalanine

To a stirred solution of N-Boc-ρ-N-propargyltrifluoroacetamido-L-phenylalanine (500 mg, 1.2 mmol) in MeOH (5 ml) was added 30% $NH_4OH$ and allowed to incubation for 4 hours. The solution was then evaporated under reduced pressure to give N-Boc-ρ-propargylamino-L-phenylalanine. $^1$H-NMR (DMSO-$d_6$) δ 7.35 (d, J=6.7 Hz, 2H, Ar), 7.21 (d, J=6.7 Hz, 2H, Ar), 6.49 (broad s, 1H, NH-Boc), 4.00 (broad s, 2H, $NH_2$), 3.75 (broad s, 2H, $CH_2$-propargylic), 3.48 (m, 1H, CH-chiral), 2.81–3.55 (m, 2H, $CH_2$Phe), 1.32 (S, 9H, t-butyl).

1.3) Preparation of ρ-propargylamido-5FAM-L-phenylalanine

To a stirred solution of N-Boc-ρ-propargylamino-L-phenylalanine (33 mg, 0.12 mmol) in anhydrous DMSO (3 ml) at room temperature under Ar atmosphere were added di-isopropylethylamine (276 ml, 1.58 mmol, 15 eq) and a 1 ml of a solution of DMSO and 5FAM-NHS ester (60 mg, 0.13 mmol, 1.2 eq). After 4 hours at room temperature the reaction mixture was subjected to HPLC with reverse-phase column and eluted with a gradient of 0.05% aqueous TFA to 0.05% TFA in $CH_3CN$ for 30 minutes. Fractions containing 5FAM labeled L-phenylalanine were dried to provide N-Boc-ρ-propargylamido-5FAM-L-phenylalanine. This compound was added to an ice cold solution of 1:1 aqueous TFA and stirred for 1 hour at room temperature to produce ρ-propargylamido-5FAM-L-phenylalanine. $^1$H-NMR ($CD_3OD$) δ 8.46 (s, 1H, Ar), 8.24 (d, J=6.7 Hz, 1H, Ar), 6.52–7.46 (m, 11H, Ar), 4.44 (s, 2H, $CH_2$-propargylic), 4.25 (m, 1H, CH-chiral), 3.06–3.19 (m, 2H, $CH_2$-phe).

1.4) Procedure for converting ρ-propargylamido-5FAM-L-phenylalanine to N-5Rhodamine-ρ-propargylamido-5FAM-L-phenylalanine (FIG. 1)

ρ-Propargylamido-5FAM-L-phenylalanine (15 mg, 0.03 mmol) was dissolved in anhydrous DMSO (2 ml) under Ar and stirred at room temperature. N,N'-di-isopropylethylamine (68 ml, 0.39 mmol, 15 eq), and 5-rhodamine dye NHS-ester (0.39 mmol, 1.2 eq) in anhydrous DMSO were added to the solution. After 1–2 hours the solution was subjected to HPLC with a reverse-phase Delta Pak C18 column (1.9×30 cm) and eluted with a gradient of 0.1M TEAA to $CH_3CN$ at 20 ml/min for 30 minutes. Fractions containing the ET-cassette were concentrated under reduced pressure.

Example 2

Figure 3:
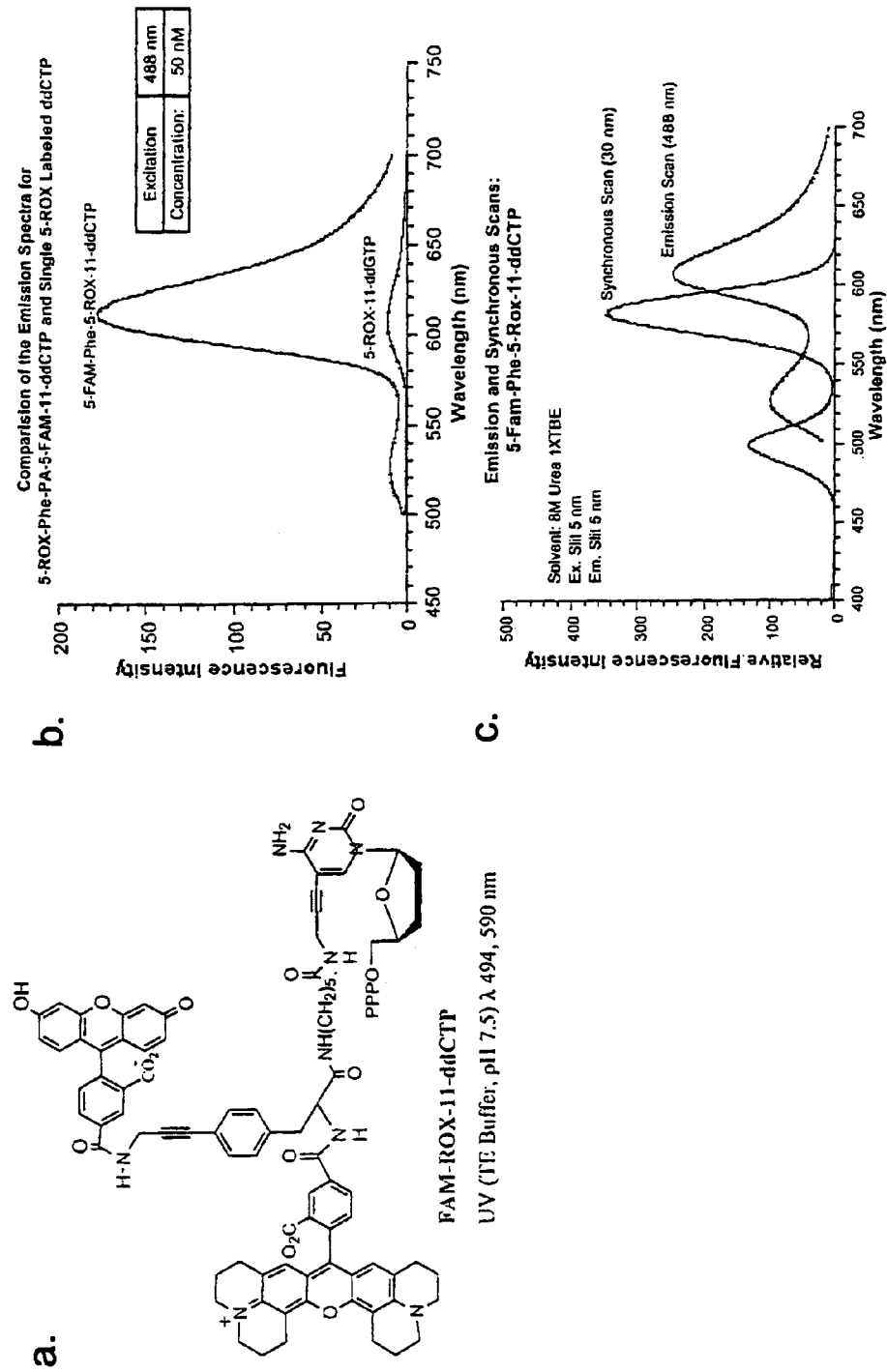
FIGS. 3a, b and c are the chemical structure (3a) and fluorescence Resonance Energy Transfer Data (3b, c) of ET Dye Terminator 5-FAM-Phe-5-ROX-11-ddCTP.
Figure 4:
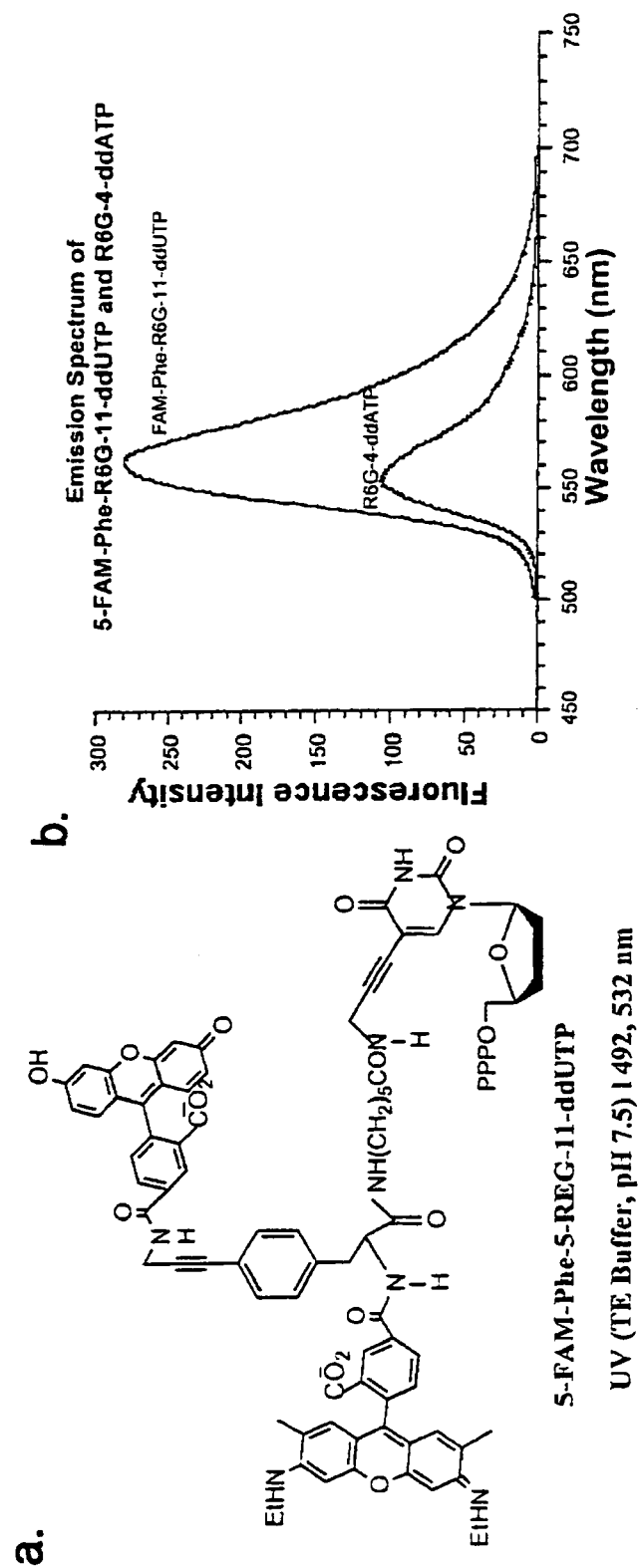
FIGS. 4a and b are the chemical structure (4a) and fluorescence Resonance Energy Transfer Data (4b) of ET Dye Terminator 5-FAM-Phe-5-REG-11-ddUTP.
Figure 5:
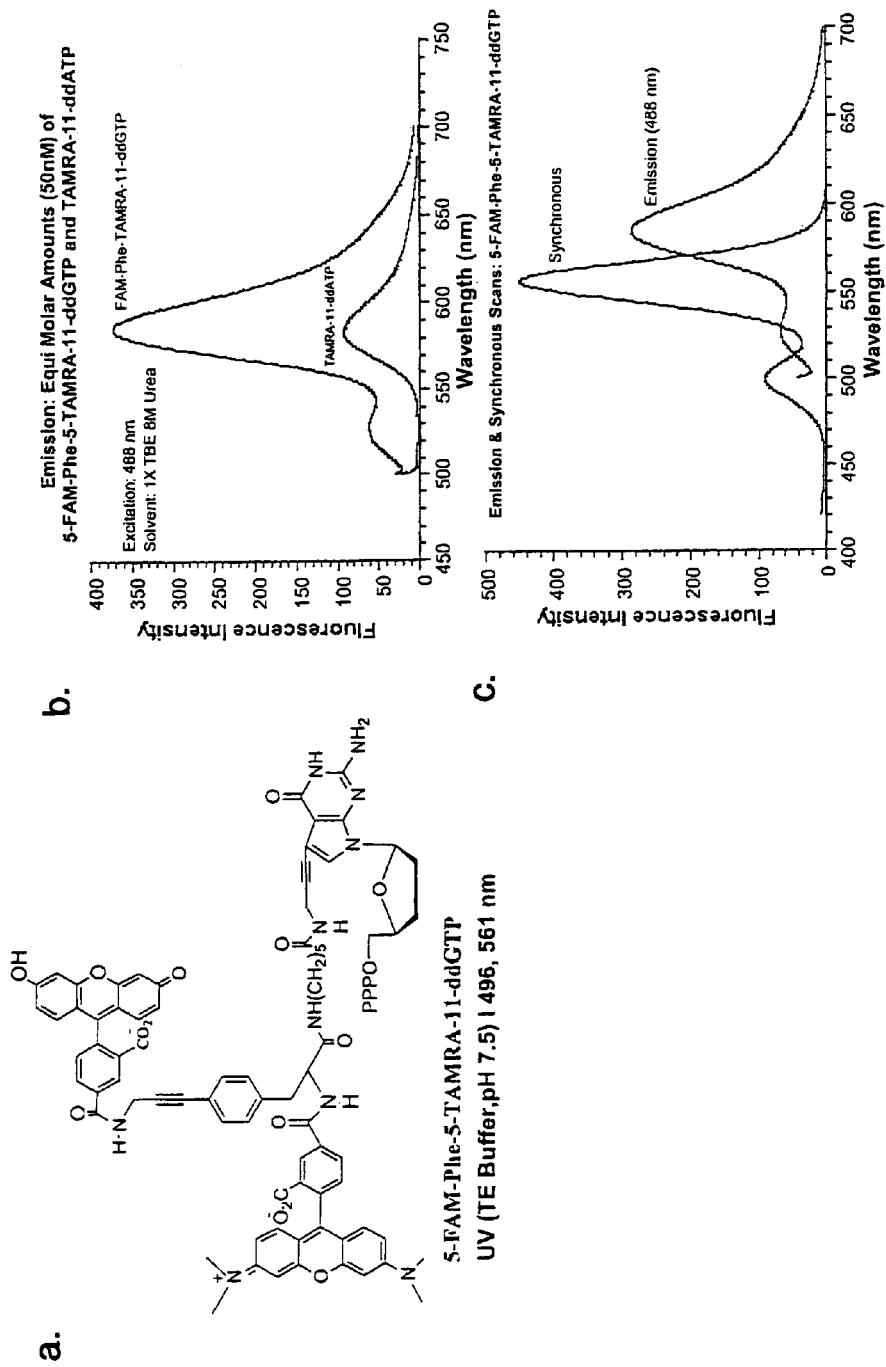
FIGS. 5a, b and c are the chemical structure (5a) and fluorescence Resonance Energy Transfer Data (5b, c) of ET Dye Terminator 5-FAM-Phe-5-TAMRA-11-ddGTP.
Figure 6:
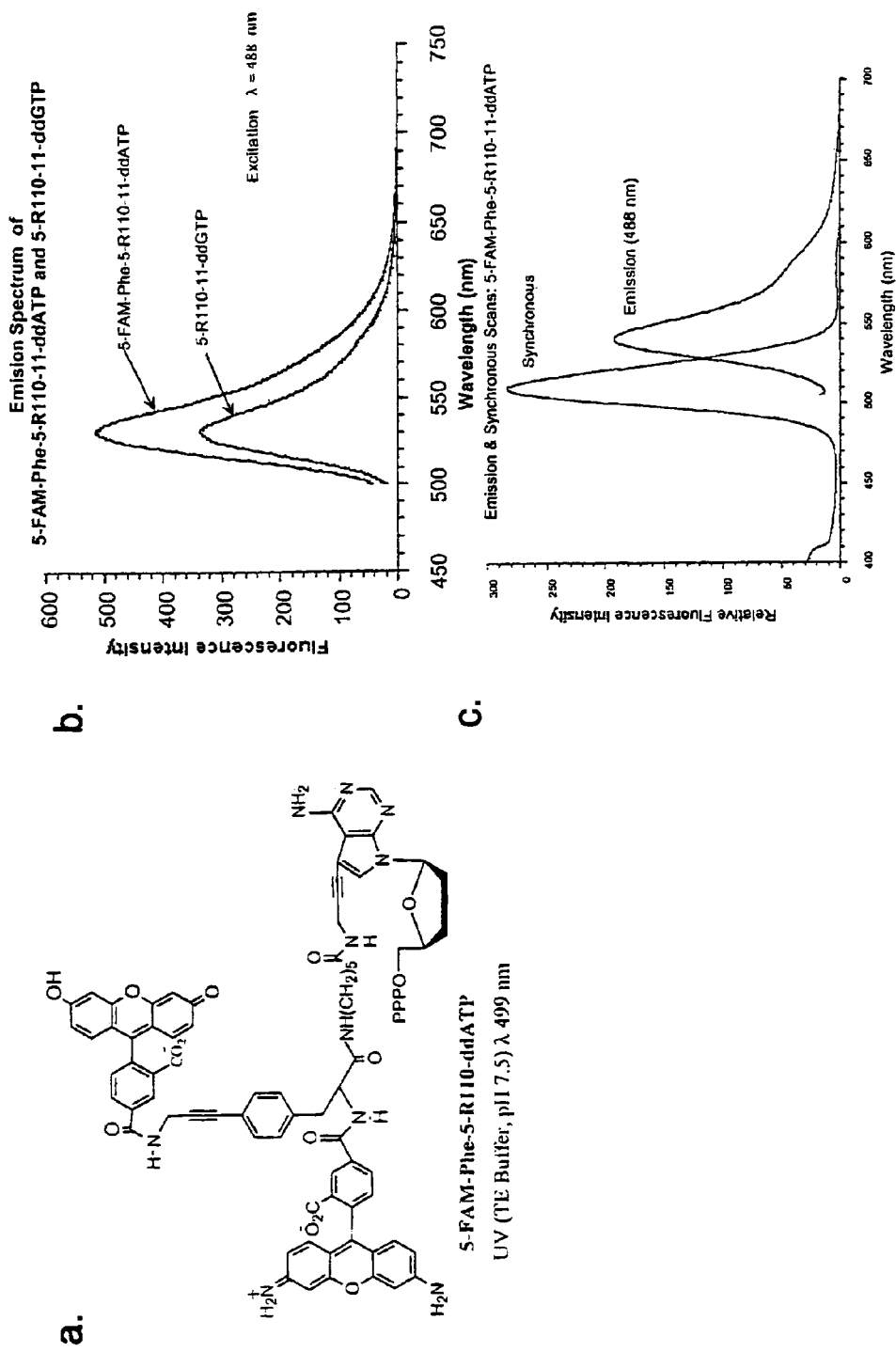
FIGS. 6a, b and c are the chemical structure (6a) and fluorescence Resonance Energy Transfer Data (6b, c) of Et Dye Terminator 5-FAM-Phe-5-R110-ddATP.

Preparation of Energy Transfer Dye Attached to a Dideoxynucleotide (5FAM-ROX-Phe-11-ddCTP) (FIGS. 1 and 3)

To a stirred solution of N-5ROX-ρ-propargylamido-5FAM-L-phenylalanine were added N,N'-disuccinimidylcarbonate and anhydrous THF solution of DMAP.

The corresponding NHS ester was formed after 20 minutes and the ester was conjugated with 5-(N-propargyl-6-aminocaproyl)ddCTP dissolved in buffer (pH 8.5). After stirring at room temperature for 1 hour, solvent and buffer were removed under reduced pressure and the residue obtained was purified by $SiO_2$ gel water aspirator vacuum column chromatography eluting with 2:8 to 1:1 MeOH in $CHCl_3$ to MeOH, thereby removing free dye and N-hydroxysuccinimide impurities. Fractions were further purified by reverse phase HPLC methods. Fluorescence enhancement of the Energy Transfer dye conjugate was shown to be 8.25 times that of single ROX-labeled ddCTP.

It would be clear using the above examples that other like biological molecules, such as deoxynucleotides and oligonucleotides, may be attached to corresponding NHS esters of the invention following the above methodology to produce compounds as exemplified in the drawings provided herein.

Example 3

Figure 7A:
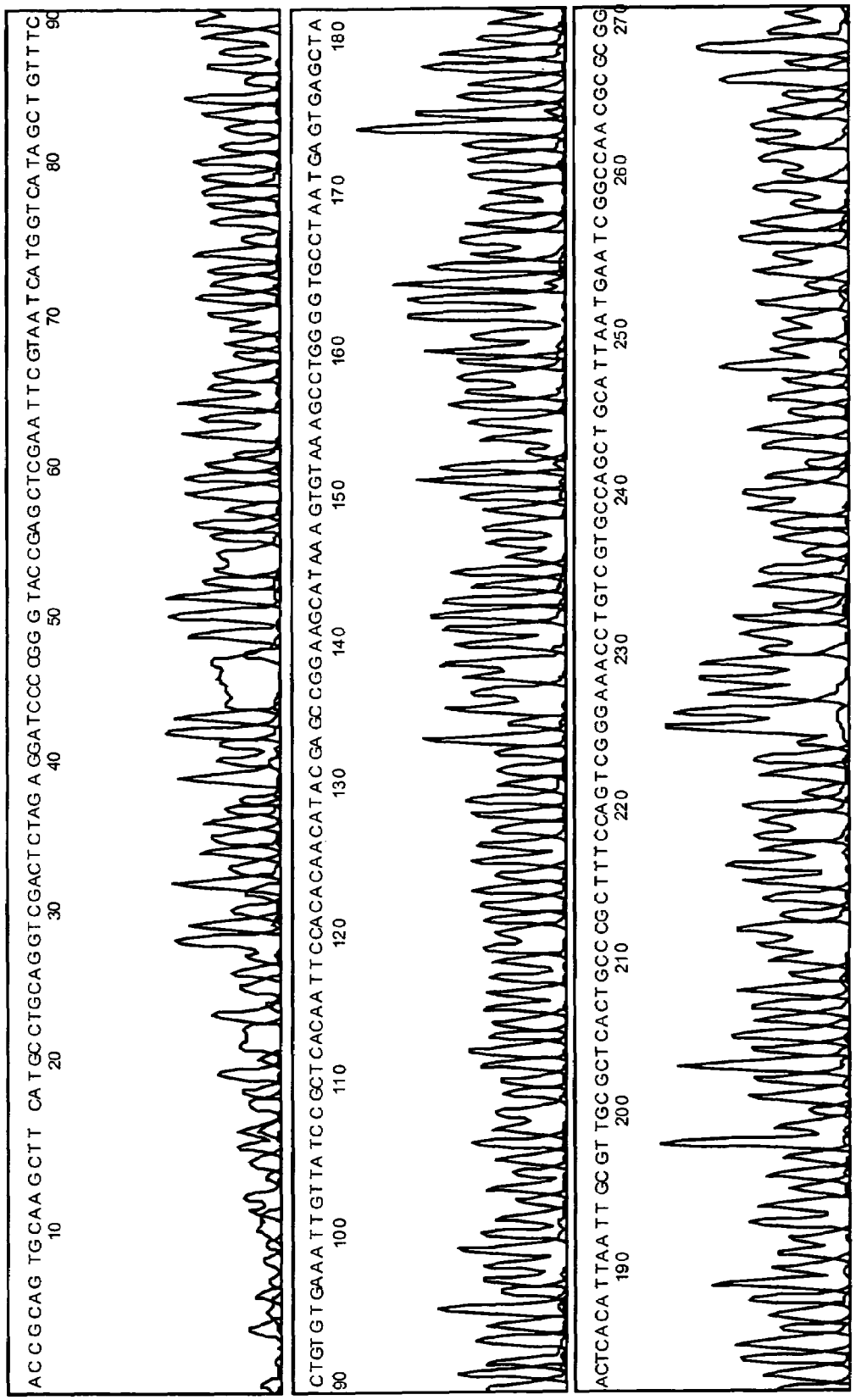
FIGS. 7a, b and c show the resulting sequencing data of a DNA molecule of Example 3 using the energy transfer dyes disclosed herein.
Figure 7B:
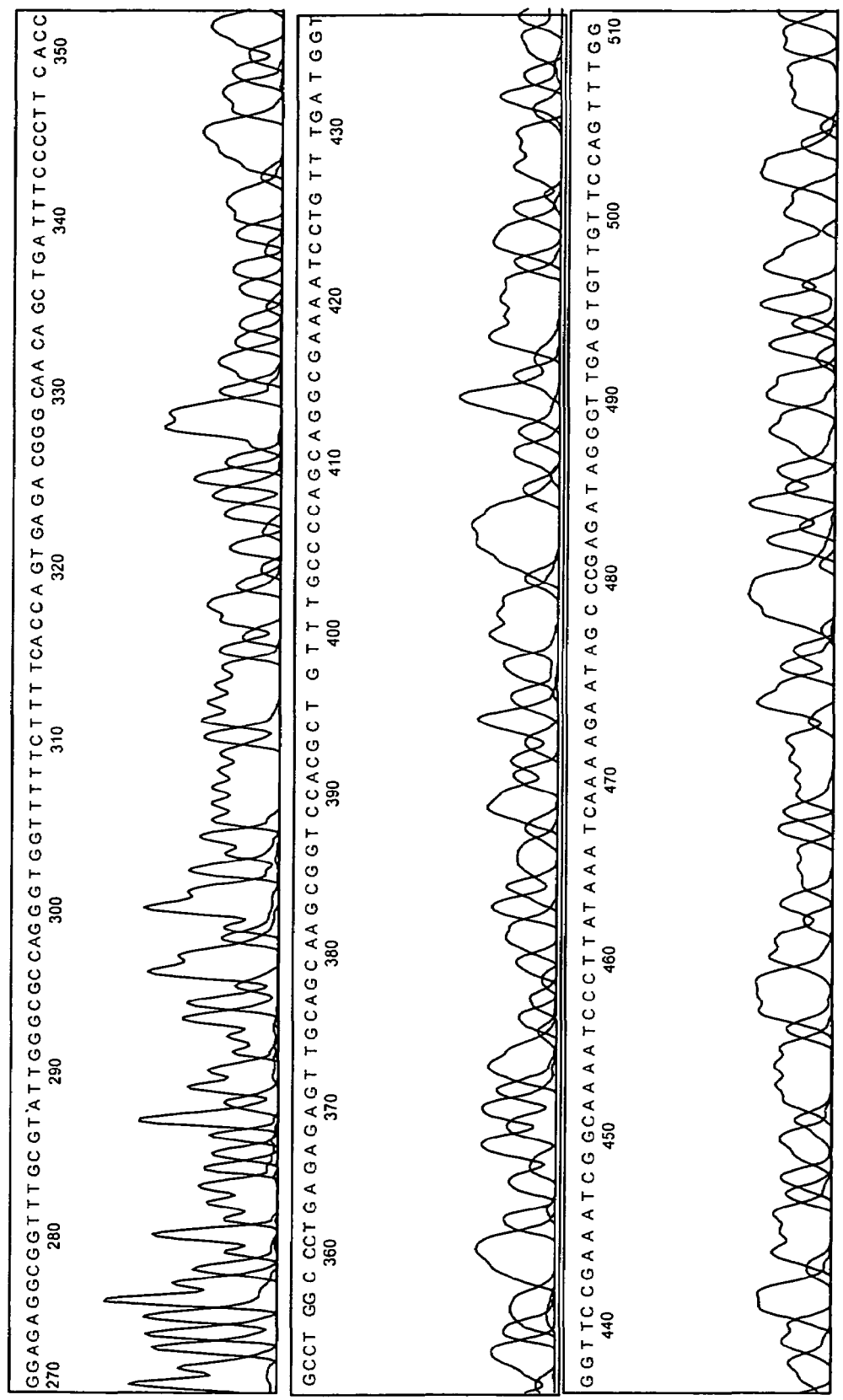
Figure 7C:
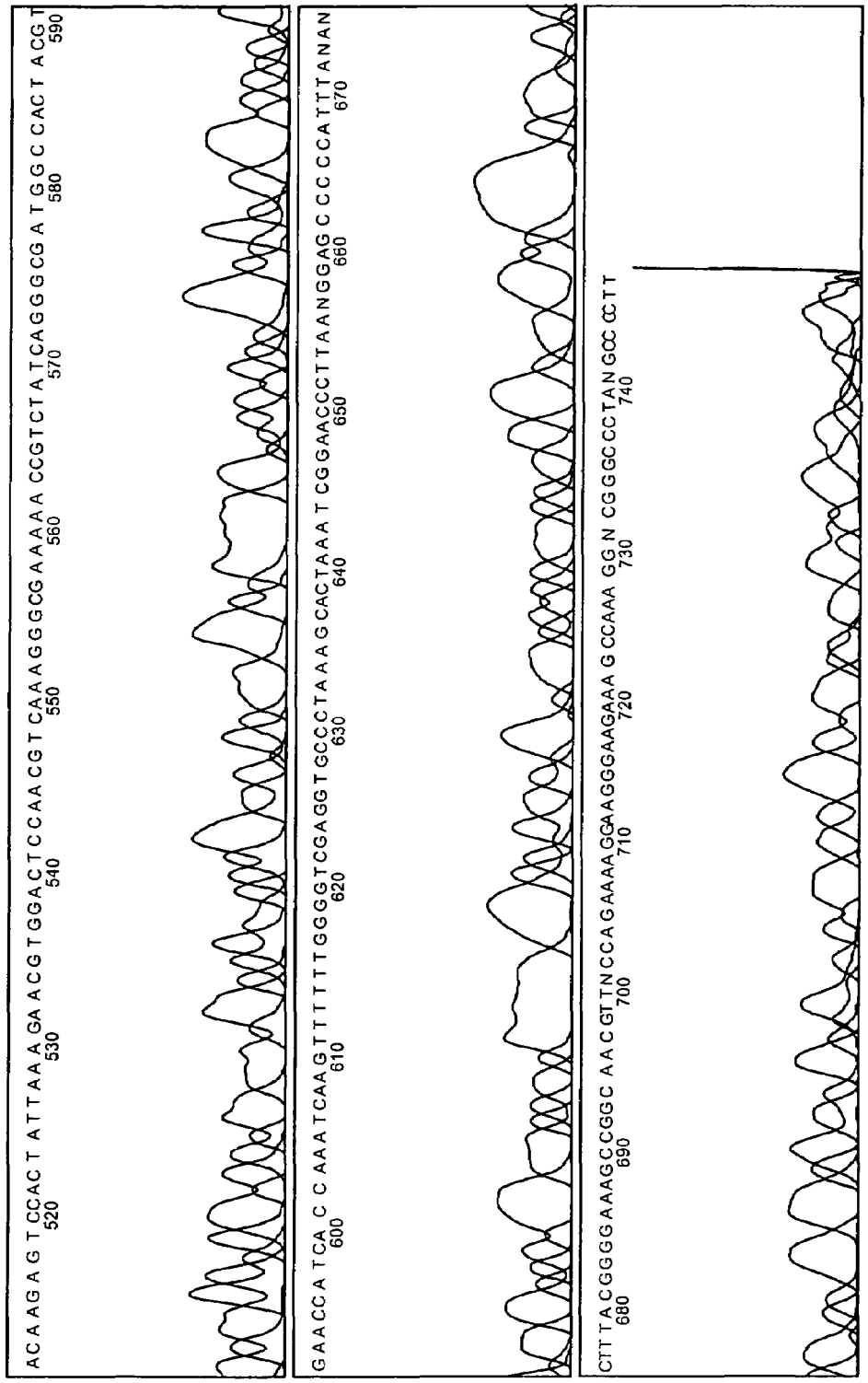
Figure 8:
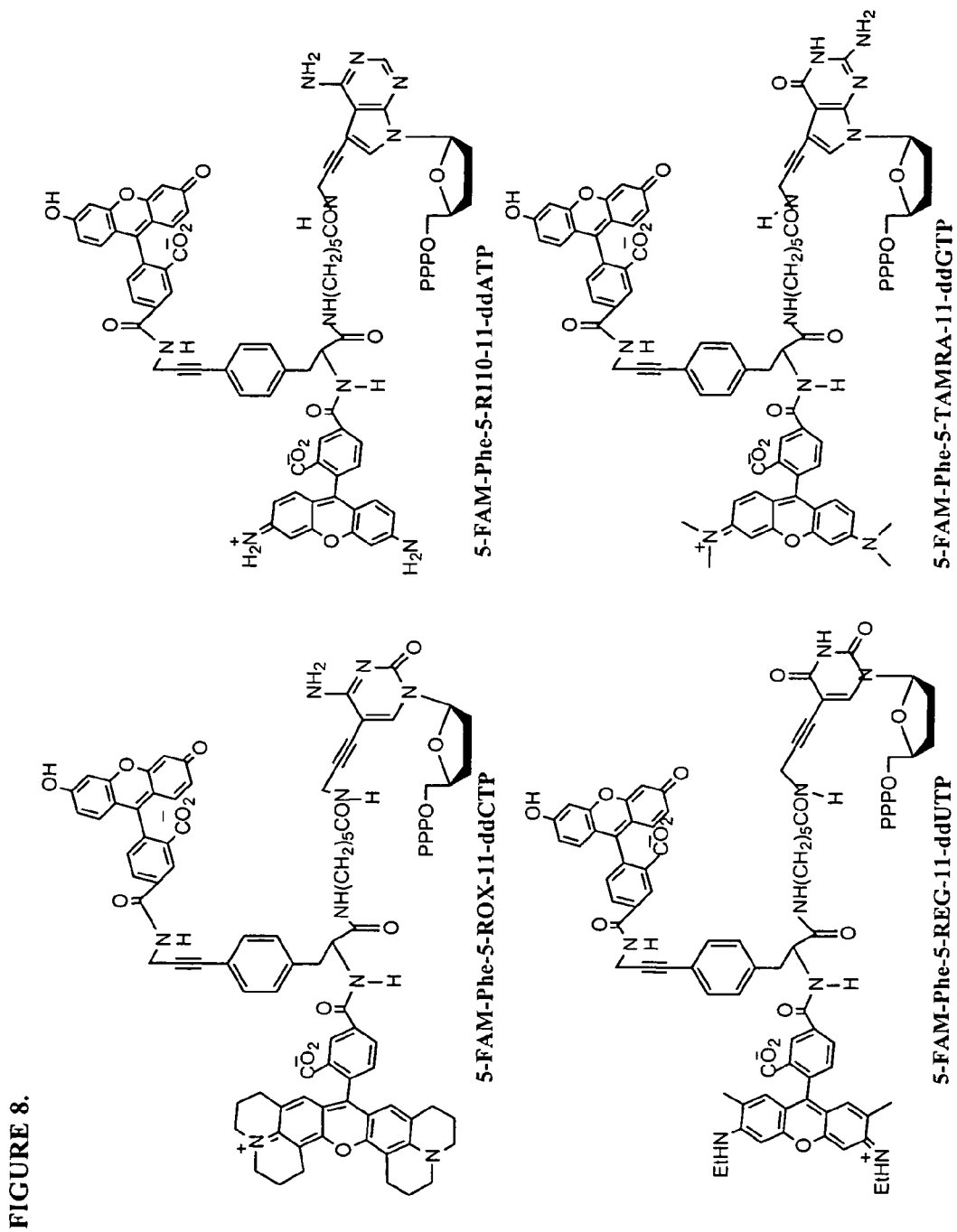
FIG. 8 is a set of four color blue-Energy Transfer Dye terminators.

Sequencing DNA Using Energy Transfer Dye Labeled Dideoxynucleoside Triphosphates (FIG. 7)

A sequence of M13mp18 template DNA was generated using standard "–40" primer. The reaction mixture (20 µl) contained 200 µM each of dATP, dCTP, and dTTP, 1000 µM dITP, 310 nM 5-FAM-Phe-5-TAMRA-11-ddGTP, 140 nM 5-FAM-Phe-5-R110-11-ddATP, 275 nM 5-FAM-Phe-5-R6G-11-ddTTP, 410 nM 5-FAM-Phe-5-ROX-11-ddCTP, 2 pmol –40 primer, 200 ng M13mp18 DNA, 20 units of Thermo Sequenase II (Amersham Pharmacia Biotech), 0.0008 units *Thermoplasma acidophilum* inorganic pyrophosphatase, 50 mM Tris-HCL pH 8.5, 35 mM KCl and 5 mM $MgCl_2$.

The reaction mixture was incubated in a thermal cycler for 25 cycles of 95° C., 30 sec; 60° C., 60 sec. After cycling, the reaction products were precipitated with ethanol using standard procedures, washed, and resuspended in formamide loading buffer. The sample was loaded on an Applied Biosystems model 377 instrument and results were analyzed using standard software methods.

It would be clear using the above examples that other like energy transfer dyes of the invention may be attached to corresponding DNA terminators and used for sequencing reactions.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The dyes, substituents, and target materials described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, those skilled in the art will readily recognize that the present energy transfer dyes can incorporate a variety of different dye moieties, linkers, attachment groups, and reactive groups, and can be attached to a variety of different target materials. Thus, such additional embodiments are within the scope of the present invention and the following claims.

The invention illustratively described herein suitably may be practiced in the absence of any element or elements, limitation or limitations, which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Thus, additional embodiments are within the scope of the invention and within the following claims.

What we claim is:

1. A compound of the formula:

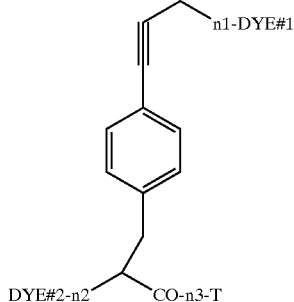

wherein n1, n2, and n3 are chains of linked atoms wherein the atoms are selected from the group consisting of carbon, oxygen, phosphorus, nitrogen and sulfur;

T is a biological molecule selected from the group consisting of antigens, drugs, peptides, polypeptides, proteins, nucleic acid molecules, nucleotides, dideoxynucleotides, ribonucleic acids, deoxyribonucleic acids, carbohydrates, lipids, antibodies, peptide nucleic acids, and locked nucleic acids, DYE #1 is a first dye moiety suitable as an acceptor or donor in an energy transfer arrangement, DYE #2 is a second dye moiety suitable as a donor or acceptor in an energy transfer arrangement with DYE #1, and DYE #1 and DYE #2 are in an energy transfer arrangement.

2. A compound of the formula:

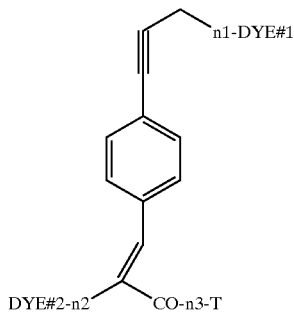

wherein n1, n2, and n3 are chains of linked atoms wherein the atoms are selected from the group consisting of carbon, oxygen, phosphorus, nitrogen and sulfur;

T is a biological molecule selected from the group consisting of antigens, drugs, peptides, polypeptides, proteins, nucleic acid molecules, nucleotides, dideoxynucleotides, ribonucleic acids, deoxyribonucleic acids, carbohydrates, lipids, antibodies, peptide nucleic acids, and locked nucleic acids, DYE #1 is a first dye moiety suitable as an acceptor or donor in an energy transfer arrangement, DYE #2 is a second dye moiety suitable as a donor or acceptor in an energy transfer arrangement with DYE #1, and DYE #1 and DYE #2 are in an energy transfer arrangement.

3. A compound of the formula:

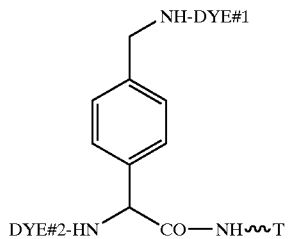

wherein T is a ddNTP or a primer,

DYE #1 is a first dye moiety suitable as an acceptor or donor in an energy transfer arrangement, DYE #2 is a second dye moiety suitable as a donor or acceptor in an energy transfer arrangement with DYE #1, and DYE #1 and DYE #2 are in an energy transfer arrangement, and NH and the squiggly line together are a chain of linked atoms wherein the atoms are selected from the group consisting of carbon, oxygen, phosphorus, nitrogen and sulfur.

4. A compound of the formula:

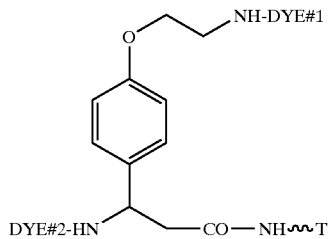

wherein T is a ddNTP or a primer,

DYE #1 is a first dye moiety suitable as an acceptor or donor in an energy transfer arrangement, DYE #2 is a second dye moiety suitable as a donor or acceptor in an energy transfer arrangement with DYE #1, and DYE #1 and DYE #2 are in an energy transfer arrangement, and NH and the squiggly line together are a chain of linked atoms wherein the atoms are selected from the group consisting of carbon, oxygen, phosphorus, nitrogen and sulfur.

5. A compound of the formula:

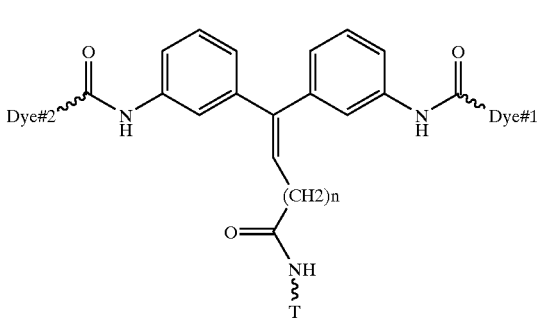

wherein T is a ddNTP or a primer, n=1–10,

DYE #1 is a first dye moiety suitable as an acceptor or donor in an energy transfer arrangement, DYE #2 is a second dye moiety suitable as a donor or acceptor in an energy transfer arrangement with DYE #1, and DYE #1 and DYE #2 are in an energy transfer arrangement, and NH—CO and the squiggly line together are a chain of linked atoms wherein the atoms are selected from the group consisting of carbon, oxygen, phosphorus, nitrogen and sulfur.

6. The compound of any of claims 1–5, wherein DYE #1 is selected from the group consisting of: 5-carboxyfluorescein, 6-carboxyfluorescein, 6-carboxy-4',5'-dichloro-2',7'-dimethoxyfluorescein, CyA (3-(ε-carboxypentyl)-3'-ethyl-5,5'-dimethyl oxacarbocyanine), Cy2(3-(ε-carboxypentyl)-3'-ethyl-oxa-carbocyanine) and Cy3 (3-)ε-carboxypentyl)-1'-ethyl-3,3,3',3'-tetramethyl-5,5'-disulphonato-carbocyanine) and Cy5 (1-(ε-carboxypentyl)-1'-ethyl-3,3,3',3'-tetramethyl-5,5'-disulphonato-dicarbocyanine, and wherein dye #1 transfers energy to dye #2.

7. The compound of any of claims 1–5, wherein DYE #2 is selected from the group consisting of: carboxyrhodamine (Rhodamine 110-5), 6-carboxyrhodamine (Rhodamine 110-6), 5-carboxyrhodamine-6G (R6G-5 or REG-5), 6-carboxyrhodamine-6G (R6G-6 or REG-6),N,N,N',N'-tetramethyl-5-carboxyrhodamine, N,N,N',N'-tetramethyl-6-carboxyrhodamine (TAMRA or TMR), 5-carboxy-X-rhodamine, 6-carboxy-X-rhodamine (ROX), Cy3 (3-(ε-carboxypentyl)-1'-ethyl-3,3,3',3'-tetramethyl-5,5-disulphonato-carbocyanine), Cy3.5 (3-(ε-carboxypentyl)-1'-ethyl-3,3,3',3'-tetramethyl-4,5,4'5'-(1,3-disulphonato) dibenzo-carbocyanine), Cy5 (1-(ε-carboxypentyl)-1'-ethyl-3,3,3',3'-tetramethyl-5,5'-disulphonato-dicarbocyanine, Cy5.5 (1-(ε-carboxypentyl)-1'-ethyl-3,3,3',3'-tetramethyl-4,5,4',5'-(1,3-disulphonato)-dibenzo-dicarbocyanine, and Cy7 (1-(ε-carboxypentyl)-1'-ethyl-3,3,3',3'-tetramethyl-5,5'-disulphonato-tricarbocyanine and wherein dye #2 transfers energy with dye #1.

* * * * *